(12) United States Patent
Zheng et al.

(10) Patent No.: US 7,449,578 B1
(45) Date of Patent: Nov. 11, 2008

(54) TWO-PHOTON ABSORBING MATERIALS WITH QUENCHED EMISSION

(75) Inventors: Qingdong Zheng, North Tonawanda, NY (US); Paras N. Prasad, Williamsville, NY (US); Guang S. He, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 493 days.

(21) Appl. No.: 11/087,236

(22) Filed: Mar. 23, 2005

Related U.S. Application Data

(60) Provisional application No. 60/555,661, filed on Mar. 23, 2004.

(51) Int. Cl.
*C07F 15/04* (2006.01)
*C07D 471/02* (2006.01)

(52) U.S. Cl. .............................. 546/10; 546/88; 430/78

(58) Field of Classification Search .................... 546/10, 546/88; 430/78
See application file for complete search history.

(56) References Cited

U.S. PATENT DOCUMENTS

| | | | |
|---|---|---|---|
| 6,300,502 B1 | 10/2001 | Kannan et al. | |
| 6,555,682 B1 | 4/2003 | Kannan et al. | |
| 6,566,529 B1 | 5/2003 | Kim et al. | |
| 6,962,995 B2 * | 11/2005 | Lecloux et al. | 546/88 |

FOREIGN PATENT DOCUMENTS

| WO | WO 99/53242 | 10/1999 |
|---|---|---|

OTHER PUBLICATIONS

Dietrich-Buchecker, C. et al.: Selective and efficient synthesis of di-, tri- and tetrasubstituted 1, 10-phenanthrolines. Tetrahed. Lett., vol. 40, pp. 3395-3396, 1999.*

Senechal et al.; Zinc(II) as a Versatile Template for the Design of Dipolar and Octupolar NLO-phores; J. Am. Chem. Soc. 2002, 124, pp. 4560-4561.

Gillies et al.; Designing Macromolecules for Therapeutic Applications: Polyester Dendrimer-Poly(ethylene oxide) "Bow-Tie" Hybrids with Tunable Molecular Weight and Architecture; J. Am. Cem. Soc. 2002; 124, pp. 14137-14146.

Dhenaut et al.; Chiral Metal Complexes with Large Octupolar Optical Nonlinearities; Nature, vol. 374, Mar. 23, 1995; pp. 339-342.

Kannan et al.; Toward Highly Active Two-Photon Absorbing Liquids. Synthesis and Characterization of 1,3,5-Triazine-Based Octupolar Molecules; J. Am. Chem. Soc., 2004, 16, pp. 185-194.

He et al.; New Technique for Degenerate Two-Photon Absorption Spectral Measurements Using Femtosecond Continuum Generation; Optics Express 566, vol. 10, No. 13, Jul. 1, 2002; pp. 566-574.

Beljonne et al.; Role of Dimensionality on the Two-Photon Absorption Response of Conjugated Molecules: The Case of Octupolar Compounds; Adv. Funct. Mater. 2002, 12 No. 9, September, pp. 631-641.

Lee et al.; Two-Photon Absorption and Nonlinear Optical Properties of Octupolar Molecules; J. Am. Chem. Soc. 2001, 123, pp. 10658-10667.

Grayson et al.; Convergent Dendrons and Dendrimers: from Synthesis to Applications; J. Am. Chem. Soc. 2001, 101, pp. 3819-3867.

* cited by examiner

*Primary Examiner*—Charanjit S Aulakh
(74) *Attorney, Agent, or Firm*—Hodgson Russ LLP

(57) ABSTRACT

The present invention provides substituted phenanthroline compounds with high two photon absorption cross sections, as well as substituted phenanthroline compounds which additionally have quenched fluorescence emission upon two photon absorption.

22 Claims, 12 Drawing Sheets

E=Donor/Acceptor, M=metal, L=Ligand, n=0,1

F-2

F-3

F-4

TWO-PHOTON ABSORBING MATERIALS WITH QUENCHED EMISSION

This application claims priority to U.S. provisional application No. 60/555,661, filed on Mar. 23, 2004, the disclosure of which is incorporated herein by reference.

FIELD OF THE INVENTION

The present invention relates to two-photon absorbing materials.

BACKGROUND OF THE INVENTION

Two-photon absorption (TPA) phenomenon, theoretically predicted by Maria Goppert-Mayer in 1931 and experimentally observed by Kaiser and Garrett in 1965, has received little consideration for practical applications until the advent of high peak-power laser systems and the availability of materials with large two-photon absorption. However, from the mid 1990's to the present, significant advances have been made in the design and synthesis of two-photon absorbing materials with very large cross-section ($\sigma_2$) values.

In the process of two-photon absorption (TPA), a transition from a molecule's ground state to an excited state occurs by simultaneous absorption of two photons which energetically sum up to the transition energy. Two photon absorption processes take place at photon energies which are outside of the absorption band corresponding to the linear, one photon absorption transition. Furthermore, the amount of two photon absorption varies quadratically with irradiation intensity, not linearly as with one one photon absorption. As a result, when a chromophore is irradiated at a typical two photon absorption wavelength, a high percentage of the incident intensity will be transmitted. However, at high intensities, as two photon absorption increases in strength, a lower percentage of the incident intensity is transmitted.

TPA-based applications at present include optical power limiting (1), up-conversion lasing (2), three dimensional fluorescence imaging (3), pulse reshaping and stabilization (4), and photodynamic therapy (5).

A current design strategy for the construction of two photon absorbing molecules is based on a three component, electronically conjugated system which electron donors (D) and electron acceptors (A). Both symmetrical and asymmetrical molecules can be designed according to this model, which have been proven to be effective to get compounds with large two-photon absorption. AF-50, a benchmark two-photon absorbing compound developed by Air Force lab, is an asymmetrical molecule. Perry and co-workers (6) have also discovered symmetrical structured chromophores with large two-photon absorption. Prasad and co-workers have developed multi-branched TPA chromophores and observed enhanced two-photon absorption.

Presently, most chromophores with efficient two-photon absorption (e.g., AF 350 and AF 389(7)) are highly fluorescent upon excitation by a strong laser beam. This feature is desirable for applications such as three dimensional fluorescence imaging, two-photon pumped lasing and two-photon biosensing. However, it is undesirable for some potential applications, including those in which fluorescence would interfere with the intended function of the material. For example, materials which fluoresce strongly are undesirable for use in optical power limiting materials which are intended for the protection of human eyes, sensors, etc. Fluorescence is also undesirable in those applications in which the energy imparted to a molecule by the two photon absorption is to be used in the performance of a function, such as, for example, two-photon induced photopolymerization or three-dimensional microfabrication. Thus, the development materials with high TPA cross section and quenched fluorescence would be welcomed in the art.

Recently, extensive efforts have been concentrated on the synthesis of π-conjugated push-pull nonlinear optical (NLO) chromophores and macroscopic assemblies, such as polymers or dendrimers(8). This rapid development is consistent with the increasing interest in chemically and thermally stable molecules with nonlinear optical or luminescent properties, such as TPA.

SUMMARY OF THE INVENTION

The present invention provides substituted, π-conjugated, 1,10-phenanthroline-containing compounds having high TPA cross sections. Further provided are metal coordinated compounds which have quenched emissions in addition to high TPA. The preparation of exemplary compounds is described in the examples.

The compounds of the present invention are phenanthroline-based compounds which exhibit strong two-photon absorption, generally in the vicinity of 800 nm. Furthermore, compounds which are formed by coordinating the phenanthroline-based compounds to nickel or other metal ions to form ion chelating complexes show not only highly active two-photon absorption but also quenched emission relative to their non-coordinated analogs.

In one embodiment, the present invention provides compounds which comprise substituted phenanthrolines in which the substituents comprise serially connected repeating chemical moieties which, optionally, terminate in an aromatic ring which, optionally, bears one or more electron donating substituents. These chromophores possess large optical nonlinearities (e.g, two-photon, or three-photon absorption) and appreciable solubility in organic solvents.

DETAILED DESCRIPTION OF THE INVENTION

Figure 1:
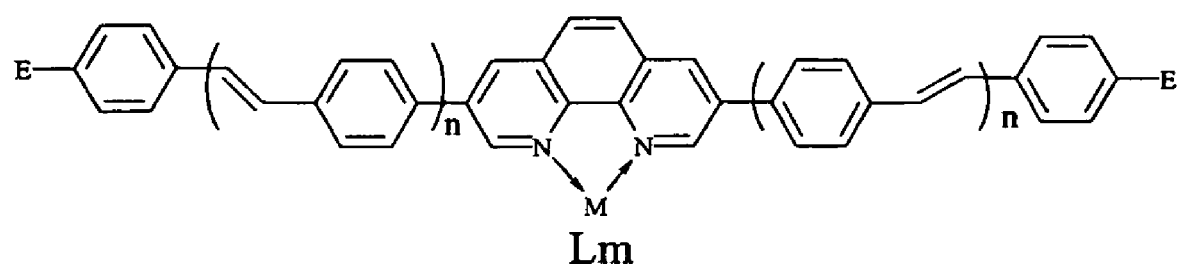
FIG. 1. Model for 1,10-phenanthroline-containing r-conjugated chromophores

The present invention provides substituted 1, 10 phenanthroline compounds with high two photon absorption cross section. In one embodiment, the compound is a phenanthroline compound which has substituents at positions 3 and 8.

Substituents which can be used include those which extend the electronic 7π-conjugation of the phenanthroline group. In an embodiment of the present invention, the phenanthroline bears substituents at the 3 and the 8 positions as shown in Formula I which include one or more of the parenthesized structure, a vinyl-bearing phenyl group, which are joined in series, as shown, optionally terminating in an aromatic ring, also shown.

The two photon cross section of compounds with substituents as shown in Formula I can generally be increased by extending the compound's π-conjugated system. For example, as n is increased in the structure below, the TPA cross section generally increases. However, compounds can become increasingly difficult to prepare as n increases. In general, compounds with an n which is 10 or less can be conveniently prepared. Compounds with an n of 1 or 0 are preferred.

The peak wavelength of the two photon absorption band can be moderated by the inclusion of one or more electron donating groups at positions in which the groups are electronically connected to the conjugated system which includes the phenanthroline, such as, for example, at one of the aromatic rings in the structure shown in Formula I. In one embodiment, the terminal aromatic ring bears one or two electron donating groups as represented by X and Y.

Electron donating groups generally have the effect of shifting the TPA peak to lower energies. The degree to which the peak is shifted generally increases with increasing donating strength. For example, substituents which are strongly electron-donating such as alkyl amino substituents will usually shift the TPA peak of a given compound more than substituents which are less strongly electron-donating, such as alkoxide or alkyl sulfide substituents. Examples of electron-donating groups which can be used in the compounds of the present invention are as follows, listed in order of increasing electron donating ability: —SR, —OR, and —NR1R2; where R, R1 and R2 can be hydrogen, hydroxyalkyl, sulfoalkyl, carboxyalkyl or unsubstituted alkyl groups.

The compounds of the present invention need not be symmetrically substituted at the phenanthroline in order to have high TPA cross sections. For example, with respect to compounds of the form illustrated in Formula I, each substituent on the phenanthroline group can have a different n, X and Y. In Formula I, X and Y are electron donating groups, n is a substituent length parameter which can be between 0 and 10, inclusive.

However, symmetrically substituted phenanthroline compounds are usually more readily prepared than asymmetrically substituted compounds. A method of preparing phenanthroline compounds as in Formula I, having symmetric substitution, is described in Examples 1-16. Three different 3,8 symmetrically-substituted compounds [3,8-Bis-{4-[2-(4-tert-butylsulfanyl-phenylvinyl]-phenyl}-[1,10] phenanthroline, 3,8-Bis-{4-[2-(3,4-bis-hexyloxy-phenyl)-vinyl]-phenyl}-[1,10] phenanthroline, and 3,8-bis-{4-[2-(N,N-dihexylaminophenyl)-vinyl]-phenyl}-[1,10]phenanthroline] are prepared in Examples 11-13.

Emission upon TPA is undesirable for many applications. However, 1,10-phenanthroline compounds possess the ability to coordinate a range of different metal ions, and the resulting metal complexes can show attractive chemical properties, including quenched fluorescence emission. An example of a phenanthroline compound according to the present invention which is coordinated with a metal is shown in Formula II. Compounds with greatly reduced TPA-associated fluorescence emission can be formed by coordinating one or two phenanthroline containing compounds to transition metal ions such as Nickel(Ni), Copper(Cu), Palladium (Pd), Ruthenium(Ru), Zinc(Zn), Iridium(Ir), Iron(Fe), Silver (Ag), etc.

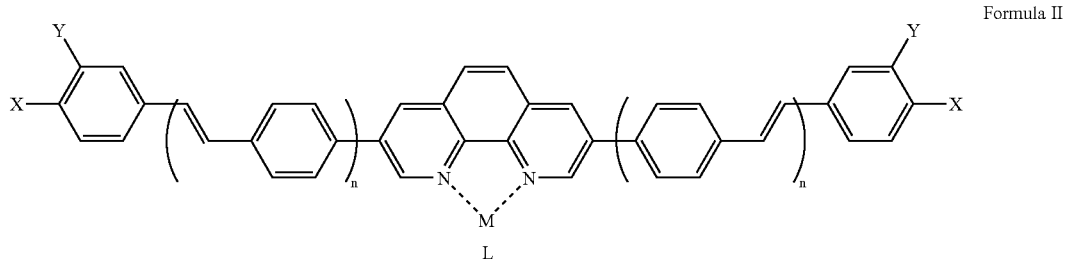

Formula II

In Formula II, X and Y are electron donating groups, n is a substituent length parameter which can be between 0 and 10, inclusive; M is a transition metal ion; and L is a ligand which is coordinated with (liganded to) the transition metal ion. As with nonmetallated compounds, each substituent on the phenanthroline group can have a different n, X and Y Without desiring to be bound by theory, it is thought that metal ions can be used as quenchers because in metal chelating complexes, the normally emissive π-π* states will decay rapidly via low-lying ligand field d-d or ring ↔metal charge transfer excited states (π–d) or (d–π*). By preparing compounds which have a 1,10-phenanthroline backbone and bear TPA-enhancing substituents, followed by chelation of the phenanthroline moieties to transition metal ions, complexes with large TPA and quenched emission may be achieved.

Ligands occur between the phenanthroline nitrogens and the metal ion. The metallated compound can comprise a Formula I:

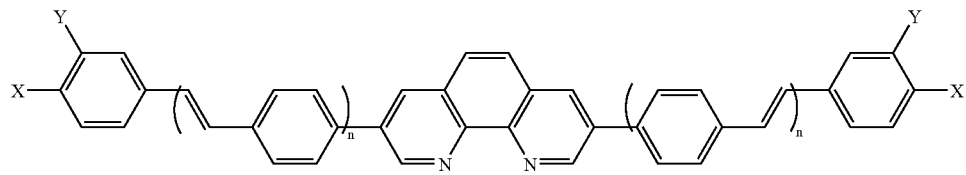

single substituted phenanthroline molecule liganded to a transition metal ion, or comprise two identical or different substituted phenanthroline compounds liganded-to a transition metal ion. The preparation of three different substituted phenanthroline metal complexes, Bis(3,8-Bis-{4-[2-(4-tert-butylsulfanyl-phenyl)-vinyl]-phenyl]-[1,10]phenanthroline) nickel(II) hexafluorophosphate, Bis(3,8-Bis-{4-[2-(3,4-bis-hexyloxy-phenyl)vinyl]-phenyl}-[1,10]phenanthroline) nickel(II) hexafluorophosphate, and Bis(3,8-bis-{4-[2-(N,N-dihexylaminophenyl)-vinyl]-phenyl}-[1,10]phenanthroline) nickel(II) hexafluorophosphate from substituted phenanthroline compounds is described in Examples 14-16. The neutral compound includes two counter anions. Examples of suitable anions are $PF_6^-$, $BPh_4^-$, $Cl^-$, $SO_4^-$, etc.

The substituted phenanthroline compounds described above can have TPA cross sections as high as $1.59*10^{-20}$ cm$^4$/GW or more at the peak TPA wavelength.

Compounds with high TPA cross section and quenched fluorescence (M-2, M-3 and M-4, for example) have far reaching implications for the field of optical data storage. Optical data storage refers to use of light for storing information in a medium, or retrieving information from the medium. Both one photon and two-photon absorbing materials can be used as optical data storage media. However, because TPA has a quadratic dependence on incident radiation intensity, rather than a linear dependence as with one photon absorption, two-photon absorption can be used to achieve highly confined spatial excitation which results in superior three-dimensional resolution.

High TPA cross section materials which also have high two-photon excited fluorescence, such as the non-metallated compounds described above (F-2, F-3 and F-4, for example), are expected to be useful in applications involving upconverted fluorescence. Upconverted fluorescence occurs through nonresonant two-photon absorption using near-IR radiation, resulting in an energy emission greater than that of the individual photons producing the excitation. The use of a longer wavelength excitation source for fluorescence emission affords advantages not feasible using conventional UV or visible fluorescence techniques. For example, the excitation beam can reach greater depths in a material without being attenuated by single photon absorption. Additionally, photobleaching is reduced. Such compounds are particularly well-suited for fluorescence detection in multilayer coatings in two-photon imaging applications.

Two-photon excitation photodynamic therapy has been investigated as an alternative to government approved one-photon excitation photodynamic therapy. In two-photon excitation, the simultaneous absorption of two photons in the near-infrared region can excite a molecule-into its singlet excited state. As in one-photon excitation photodynamic therapy, the excited molecule can undergo intersystemr crossing into its triplet state from which the photodynamic therapy effect occurs. Two-photon excitation provides the advantages of working with a smaller more confined treatment area and penetrating deeper into diseased tissues.

With respect to the examples below, $^1$H NMR spectra were run at either 300, 400, or 500 MHz. and $^{13}$C NMR at either 75 or 125 MHz in CDCl$_3$. High-resolution mass spectral determinations were carried out at 70 eV. All chemicals are commercially available from Lancaster Synthesis or the Aldrich Chemical Co. and were used as received unless stated otherwise.

EXAMPLE 1

4-tert-butylthiobenzaldehyde

To a solution of t-butylthiol (22.5 g, 0.25 mol) in 80 ml of DMSO containing potassium carbonate (33.0 g, 0.24 mol), 4-fluorobenzaldehyde (30.0 g, 0.24 mol) was added and the mixture was heated at 100° C. for 3 hours with stirring. After cooling the reaction mixture was poured into water, and the mixture was extracted with ether. The extracts were dried by MgSO$_4$ and evaporated to dryness. Distillation of the residue gave 42.0 g 4-tert-butylthiobenzaldehyde (90% yield). $^1$H NMR (500 MHz, CDCl$_3$): δ 10.03 (s, 1H), 7.83 (d, 2H, J=8.0 Hz), 7.69 (d, 2H, J=8.0 Hz), 1.34 (s, 9H).

EXAMPLE 2

3,4-Bis-hexyloxy-benzaldehyde 3,4-Dihydroxy-benzaldehyde (2.1 g, 0.015 mol), K$_2$CO$_3$ (4.0 g, 0.03 mol) and 1-iodohexane (6.4 g, 0.03 mol) were stirred in 100 ml of 1-butanol under reflux for 24 h. After cooling, the 1-butanol was removed by rotary evaporation. The residue was dissolved in 200 ml of ether, washed with water (dist.) and brine. The solution was dried over Na$_2$SO$_4$ and the solvent was removed to yield 3.7 g 3,4-Bis-hexyloxy-benzaldehyde (85%) as a dark solid. $^1$H NMR (400 MHz, CDCl$_3$): δ 9.83 (s, 1H), 7.41 (m, 2H), 6.95 (d, 1H, J=8.5 Hz), 4.07 (m, 4H), 1.85 (m, 4H), 1.48 (m, 4H), 1.35 (m, 8H), 0.91 (m, 6H).

EXAMPLE 3

4-Formyl-N,N-dihexylaniline

Anhydrous DMF (8.8 g, 0.12 mol) was cooled in an ice-water bath, and then phosphorous oxychloride (4 ml, 0.04 mol) was added dropwise with stirring from a syringe placed through the rubber septum. A bright yellow Vilsmeier-Haack reagent was formed. N,N-diheylaniline (9.1 g, 0.035 mol) was added quickly to the Vilsmeier-Haack reagent. After stirring for 30 minutes, the mixture was heated at 90° C. for one night. Then the mixture was cooled and poured into an ice water-sodium acetate solution with vigorous stirring. The product was extracted from water with ethyl ether. The organic portion was washed with a 5% K$_2$CO$_3$ aqueous solution (100 ml) to remove any remaining acid in the ethyl ether and then dried over anhydrous MgSO$_4$. The organic phase was dried over MgSO$_4$ and evaporated in vacuum before a purification by chromatography on silica gel (eluent: Ethyl acetate, petroleum: 1:2) to give a yellow oil (8.8 g, 87% yield). $^1$H NMR (400 MHz, CDCl$_3$): δ 9.69 (s, 1H, CHO); 7.69 (d, 2H, J=8.8 Hz); 6.63 (d, 2H, J=8.8 Hz); 3.34 (t, 4H, J=6.4 Hz); 1.59 (m, 4H); 1.32 (m, 12H); 0.89 (t, 6H, J=6.4 Hz).

EXAMPLE 4

(4-bromobenzyl)diethyl phosphonate

A mixture of triethyl phosphite (2.54 g, 15.3 mmol) and 4-bromobenzyl bromide (2.00 g, 10.2 mmol) was stirred at 160° C. for 2 h. During this period ethyl bromide was distilled from the reaction mixture. Subsequently, the mixture was cooled to 70° C. and the excess of triethyl phosphite was removed by distillation under reduced pressure. The product was used without further purification, yielded 92% product. $^1$H NMR (400 MHz, CDCl$_3$): δ 1.25 (t, 6H, J=7.2 Hz), 3.06, 3.11 (s, 2H), 4.01 (m, 4H), 7.16 (d, 2H, J=8.4 Hz), 7.42 (d, 2H, J=8.4 Hz).

EXAMPLE 5

4-bromo-4'-(N,N-di-n-hexylamino)stilbene

To,(4-bromobenzyl)diethyl phosphonate (0.025 mol) in 100 ml of dry THF was added sodium tert-butoxide (0.05 mol). The reaction mixture was cooled to 0° C. in an ice bath. Formyl-N,N-dihexylaniline (0.02 mol) were added to the solution, the ice bath was removed and the mixture was stirred at room temperature for 12 h. The product was poured into 200 ml of water and then THF was removed. The crude product (8.0 g, 90% yield) was collected by filtration. $^1$H NMR (400 MHz, CDCl$_3$): δ 7.41 (d, 2H, J=8.8 Hz), 7.35 (d, 4H, J=8.4 Hz), 7.31 (d, 2H, J=8.4 Hz), 6.99 (d, 1H, J=16.0 Hz), 6.78 (d, 1H, J=16.0 Hz), 6.61 (d, 2H, J=8.8 Hz), 3.27 (t, 4H, J=7.6 Hz), 1.56 (m, 4H), 1.32 (m, 12H), 0.90 (t, 6H, J=6.4 Hz), HRMS calcd. for C$_{26}$H$_{36}$BrN 441.2026, found 441.2021.

EXAMPLE 6

4-bromo-4'-tert-butylstilbene

By the same procedure as used for Example 5. Yield 78%. $^1$HNMR (400 MHz, CDCl$_3$). δ 7.47 (m, 6H), 7.38 (d, 2H, J=8.1 Hz), 7.07 (s, 2H), 1.30 (s, 9H). HRMS calcd. for C$_{18}$H$_{19}$BrS 348.0365, found 348.0372.

EXAMPLE 7

4-Bromo-3'4'-bis-hexyloxystilbene

By the same procedure as used for Example 5. Yield 90%. $^1$H NMR (400 MHz, CDCl$_3$). δ 7.45 (d, 2H, J=8.4 Hz), 7.34 (d, 2H, J=8.4 Hz), 7.02 (m, 3H), 6.85 (d, 2H, J=16.4 Hz), 4.03 (m, 4H), 1.84 (m, 4H), 1.48 (m, 4H), 1.34 (m, 8H), 0.91 (m, 6H). HRMS calcd. for C$_{26}$H$_{35}$BrO$_2$ 458.1815, found 458.1814.

EXAMPLE 8

4-Boronic acid-4'-(N,N-di-n-hexylamino)stilbene

A solution of 4-bromo-4'-(N,N-di-n-hexylamino)stilbene (13.3 g, 0.03 mol) in dry THF (100 ml)was cooled to −78° C. To this solution n-BuLi (14.4 ml, 2.5 M in hexane, 0.036 mol) was added dropwise through dropping funnel. The mixture was stirred at this temperature and after 3 hours trimethyl borate (7.8 g, 0.075 mol) dissolved in 20 ml of dry THF was added dropwise. The solution was allowed to warm to room temperature overnight. The reaction was quenched with dilute HCl (20%, 50-ml). The product was extracted with chloroform and dried over Na$_2$SO$_4$. After filtration and removal of the solvent in vacuum, the product was passed through a silica gel column (CH$_2$Cl$_2$/MeOH 10:1), and a light yellow solid was obtained. (3.0 g, 21% yield). $^1$H NMR (400 MHz, CDCl$_3$). δ 8.19 (2H, d, J=8.0 Hz), 7.59 (d, 2H, J=8.0 Hz), 7.43 (d, 2H, J=8.0 Hz), 6.64 (d, 2H, J=8.0 Hz), 7.18 (d, 1H, J=16.5 Hz), 6.95 (d, 1H, J=16.5 Hz), 3.30 (t, 4H, J=6.4 Hz), 1.58 (m, 4H), 1.33 (m, 12H), 0.90 (t, 6H, J=6.4 Hz). HRMS calcd. for (M+H$^+$) 408.3078, found 408.3074.

EXAMPLE 9

4-boronic acid-4'-tert-butylstilbene

By the same procedure as used for Example 8. Yield 75%. $^1$H NMR (300 MHz, CDCl$_3$): δ 8.25 (d, 2H, J=7.5 Hz), 7.67 (d, J=7.5 Hz, 2H), 7.53 (d, 2H, J=7.8 Hz), 7.48 (d, 2H, J=7.8 Hz), 7.17 (d, 2H, J=16.5 Hz), 1.30 (s, 9H).

EXAMPLE 10

4-Boronic-3'4'-bis-hexyloxystilbene

By the same procedure as used for Example 8. Yield: 40%. $^1$H NMR (300 MHz, CDCl$_3$): δ 8.22 (d, 2H, J=7.8 Hz), 7.63 (d, 2H, J=7.8 Hz), 7.19 (d, 1H, J=16.2 Hz), 7.04 (d, 1H, J=16.2 Hz), 7.11 (m, 2H), 6.88 (d, 1H, J=8.1 Hz), 4.03 (m, 4H), 1.85 (m, 4H), 1.49 (m, 4H), 1.35 (m, 8H), 0.92 (m, 6H).

EXAMPLE 11

3,8-Bis-{4-[2-(4-tert-butylsulfanyl-phenyl)-vinyl]-phenyl}-[1,10]phenanthroline (F-2)

A stirred solution of 3,8-dibromo-1,10-phenanthroline (0.67 g, 2 mmol), 4-boronic acid-4'-tert-butylstilbene (5 mmol), Pd(PPh$_3$)$_4$ (0.10 g, 0.09 mmol) and Na$_2$CO$_3$ (1.47 g, 10 mmol) in toluene (6 ml) and H$_2$O (3 ml) was heated to reflux under Ar atmosphere for 24 h. When the reaction was completed, water was added to quench the reaction. The product was extracted with CH$_2$Cl$_2$. The organic layer was collected, dried over anhydrous MgSO$_4$ and evaporated under vacuum. The crude solid was purified by chromatography on silica gel, using CH$_2$Cl$_2$/CH$_3$CN (10/1) as the eluent to give compound F-2 (0.99 g, 70% yield). $^1$HNMR (300 MHz, CDCl$_3$): 9.45 (d, 2H, J=1.8 Hz), 8.36 (d, 2H, J=1.8 Hz), 7.85 (s, 2H), 7.78 (d, 4H, J=7.8 Hz), 7.71 (d, 4H, J=7.8 Hz), 7.55 (d, 4H, J=8.4 Hz), 7.51 (d, 4H, J=8.4 Hz), 7.19 (s, 4H), 1.32 (s, 18H). $^{13}$C NMR (75-MHz, CDCl$_3$): δ 31.00, 46.26, 126.56, 127.13, 127.43, 127.73, 128.50, 128.73, 132.37, 132.95, 135.08, 136.70, 137.29, 137.47, 137.74, 145.08, 149.26. HRMS calcd. for C$_{48}$H$_{44}$N$_2$S$_2$ 712.2940, found 712.2954. Elemental analyses, calcd. for C$_{48}$H$_{44}$N$_2$S$_2$: C, 80.86; H, 6.22; N, 3.93, found. C, 81.09; H, 6.15; N, 3.94.

EXAMPLE 12

3,8-Bis-{4-[2-(3,4-bis-hexyloxy-phenyl)vinyl]-phenyl}-[1,10]phenanthroline (F-3)

By the same procedure as used for Example 11. Yield 52%. $^1$HNMR (500 MHz, CDCl$_3$): δ 9.48 (d, 2H, J=3.0 Hz), 8.43 (d, 2H, J=3.0 Hz), 7.90 (s, 2H), 7.80 (d, 2H, J=8.4 Hz), 7.68 (2H, d, J=8.0 Hz), 6.89 (d, 2H, J=8.4 Hz), 7.14 (d, 2H, J=16.0 Hz), 7.06 (d, 2H, J=16.0 Hz), 4.09 (t, 4H, J=6.8 Hz), 4.04 (t, 4H, J=6.8 Hz), 1.85 (m, 8H), 1.40 (m, 8H), 1.35 (m, 16H), 0.92 (m, 12H). $^{13}$C NMR (125 MHz, CDCl$_3$): δ 14.02, 14.04, 22.61, 22.62, 25.69, 25.73, 29.22, 29.30, 31.60, 31.61, 69.20, 69.33, 111.47, 113.55, 120.26, 125.63, 127.02, 127.09, 127.63, 128.46, 129.44, 130.16, 132.85, 135.13, 137.82, 144.96, 149.25, 149.37. HRMS calcd. for C$_{64}$H$_{76}$O$_4$N$_2$ 936.5800 found 936.5834. Elemental analysis, cacld. for C$_{64}$H$_{76}$N$_2$O$_4$: C, 82.01; H, 8.17; N, 2.99; found. C, 81.92; H, 8.21; N, 3.02.

EXAMPLE 13

3,8-bis-{4-[2-(N,N-dihexylaminophenyl)-vinyl]-phenyl}-[1,10]phenanthroline (F-4)

By the same procedure as used for Example 11. Yield 56%. $^1$H NMR (500 MHz, CDCl$_3$): δ 9.46 (2H, d, J=2.0 Hz), 8.38.(2H, d, J=2.0 Hz), 7.85 (s, 2H), 7.75 (4H, d, J=8.5 Hz), 7.63 (4H, d, J=8.5 Hz), 7.42 (d, 2H, J=9.0 Hz), 7.13 (2H, d, J=16.5 Hz), 6.94 (2H, d, J=16.5 Hz), 6.64 (4H, d, J=9.0 Hz), 3.29 (8H, t, J=7.5 Hz), 1.60 (8H, m), 1.33 (m, 24H), 0.91 (12H, t, J=7.0 Hz). $^{13}$C NMR (125 MHz, CDCl$_3$): δ 14.06, 22.69, 26.83, 27.26, 31.73, 51.06, 111.56, 122.57, 124.13, 126.69, 127.07, 127.57, 127.95, 128.47, 129.80, 132.73, 135.26, 135.29, 138.61, 144.92, 147.96, 149.29 HRMS calcd. for C$_{64}$H$_{78}$N$_4$ 902.6221, found 902.6250. Elemental analysis, calcd. for C$_{64}$H$_{79}$N$_4$: C, 85.09; H, 8.70; N, 6.20 found. C, 84.59; H, 8.51; N, 6.24.

EXAMPLE 14

Bis(3,8-Bis-{4-[2-(4-tert-butylsulfanyl-phenyl)-vinyl]-phenyl}-[1,10]phenanthroline)nickel(II) hexafluorophosphate Ni(F-2)$_2$(PF$_6$)$_2$ (M-2)

0.356 g (0.5 mmol) 3,8-Bis-{4-[2-(4-tert-butylsulfanyl-phenyl)-vinyl-phenyl}-[1,10]phenanthroline and 0.059 g (0.25 mmol) NiCl$_2$.2H$_2$O was dissolved in 25 ml dichloromethane and then stirred for 8 hours under reflux. After cooling down to room temperature, an aqueous solution (10 ml) of NaPF$_6$ (0.168 g, 0.5 mmol) was slowly added. Dichloromethane was removed and 50 ml of hexane was added, and the desired complex was precipitated. The red powder (0.39 g, 89% yield) was filtered off, washed with water and dried under vacuum. $^1$H NMR (500 MHz, CD$_2$Cl$_2$): δ 8.87 (4H, br), 8.49 (4H, br), 8.26 (4H, br), 7.74 (8H, br), 7.52-7.22 (24H, m), 6.94-6.73 (8H, m), 1.28 (36H, s) FAB, (M-2PF$_6$): 1482.2 calcd, 1482.5. Elemental analysis, calcd. for C$_{96}$H$_{88}$F$_{12}$N$_4$NiP$_2$S$_4$.C, 64.97; H, 5.00; N, 3.16, found. C, 64.68; H, 5.35; N, 3.72.

EXAMPLE 15

Bis(3 8-Bis-{4-[2-(3,4-bis-hexyloxy-phenyl)-vinyl]-phenyl}-[1,10]phenanthroline)nickel(II) hexafluorophosphate Ni(F-3)$_2$(PF$_6$) (M-3)

By the same procedure as used for Example 14. Yield 91%. $^1$H NMR (500 MHz, CDCl$_3$): δ 8.83 (4H, br), 8.15 (4H, br), 7.67 (4H, br), 7.34 (4H, br); 7.02-6.59 (32H, br), 4.05 (16H, m), 1.89 (16H, m), 1.32-1.60 (48H, br). 0.89 (24H, t) FAB, (M-2PF$_6$): 1931.8 calcd, 1931.1. Elemental analysis, calcd. for C$_{128}$H$_{152}$F$_{12}$N$_4$NiO$_8$P$_2$: C, 69.15; H, 6.89; N, 2.52. found. 69.30; H, 6.70; N, 2.62.

EXAMPLE 16

Bis(3,8-bis-{4-[2-(N,N-dihexylaminophenyl)-vinyl]-phenyl}-[1,10]phenanthroline)nickel(II) hexafluorophosphate Ni(F-4)$_2$(PF$_6$)$_2$ (M-4)

By the same procedure as used for Example 14. Yield 93%. $^1$H NMR (500 MHz, CDCl$_3$): δ 8.75 (4H, br), 8.22 (4H, br), 8.07 (4H, br), 7.63 (8H, br), 7.46 (8H, br), 7.19 (8H, br), 6.78 (8H, br), 6.54 (8H, br). 3.30 (16H, d); 1.59 (16H, d), 1.32 (48H, d), 0.90 (24H, d) FAB, (M−2 PF$_6$): 1863.2 calcd, 1863.2. Elemental analysis: calcd. for C$_{128}$H$_{156}$F$_{12}$N$_8$NiP$_2$: C, 71.33; H, 7.30; N, 5.20, found. C, 71.36; H, 7.20; N, 5.42

EXAMPLE 17

The one and two photon absorption of these compounds, as well as quenching due to metallation, are shown in FIGS. 6-12. Linear absorption spectra were recorded on a Shimadzu UV-3101 PC spectrophotometer using dilute solutions (10$^{-5}$ M in CHCl$_3$). By using different electron donors, tunable linear absorption (357 nm to 415 nm) was achieved. The metal ion chelating complexes possess red-shifted absorption compared to their metal-ion free analogs.

Figure 9:
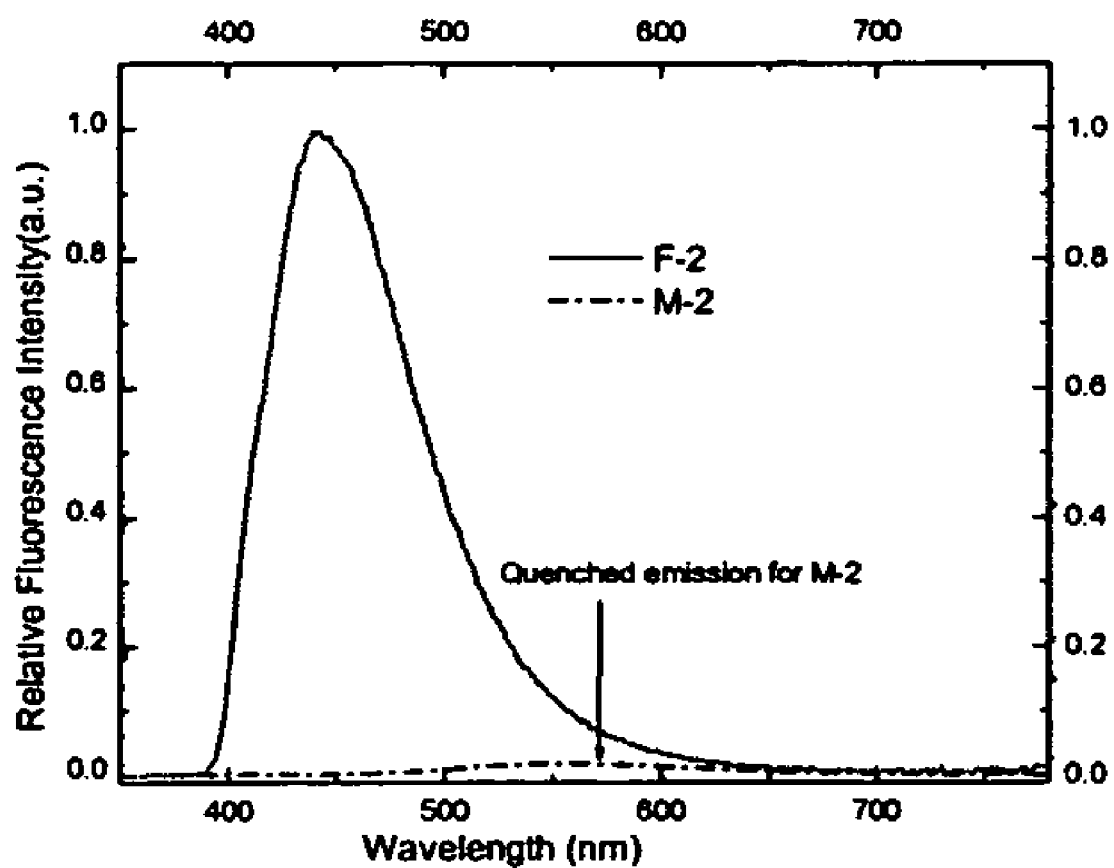
FIG. 9. One photon excited fluorescence spectra for compounds F-2, M-2
Figure 10:
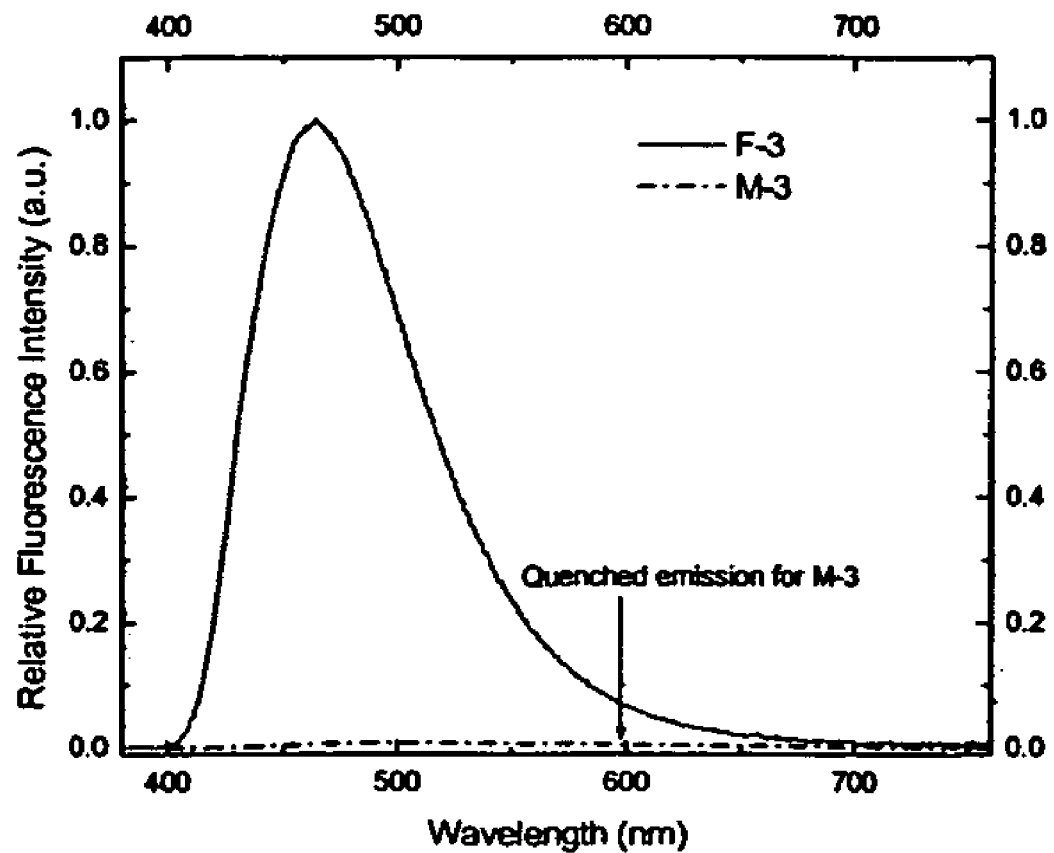
FIG. 10 One photon excited fluorescence spectra for compounds F-3, M-3
Figure 11:
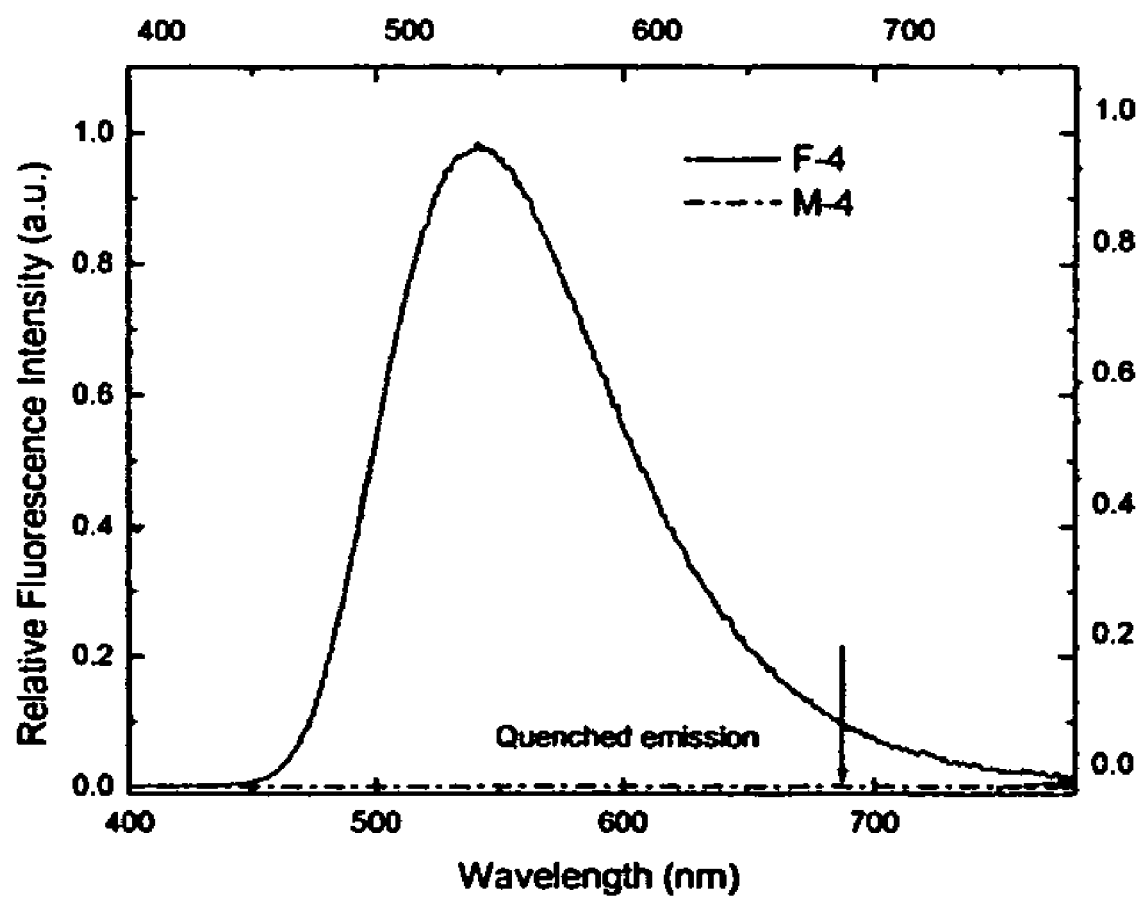
FIG. 11. One photon excited fluorescence spectra for compounds F-4, M-4

One-photon excited fluorescence was measured by using a Jobin-Yvon Fluorog FL-311 spectrofluorometer in CHCl$_3$ dilute solutions (5×10$^{-6}$ M). The emission maxima for compounds F-2, F-3, F-4 vary from 445 nm to 541 nm depending upon electron donor. As shown in FIGS. 9, 10, 11, while compounds F-2, F-3 and F-4 have strong one-photon fluorescence, their metal-ion chelating complexes have only negligible fluorescence. Absorption and fluorescence emission data are tabulated in Table 1.

TABLE 1

One and Two Photo Absorption and Fluorescence Data[a]

| Compounds | Absorption λ max (nm) | ε (×10$^4$ M$^{-1}$ cm$^{-1}$) | Emission λ max (nm) | TPA λ max (nm) | Maximum TPA cross-section σ$_2$[b] |
|---|---|---|---|---|---|
| F-2 | 357 | 8.4 | 445 | 696 | 0.58 |
| M-2 | 392 | 12.4 | 550 | 760 | 2.20 |
| F-3 | 376 | 9.4 | 466 | 758 | 0.61 |
| M-3 | 411 | 15.7 | 550 | 789 | 2.26 |
| F-4 | 415 | 9.6 | 541 | 788 | 1.59 |
| M-4 | 369 | 22.1 | 590 | 839 | 2.50 |

[a]The concentration of the solution samples for linear absorption and emission is fixed at 10$^{-5}$ M in CHCl$_3$; The concentrations of the solution samples for two-photon absorption and emission are 0.01 M (for F-2, M-2, M-3 and M-4) and 0.02 M (for F-3 and F-4). Each solution sample was filtered through a 0.2 μm Gelman acrodisc CR filter
[b]in 10$^{-20}$ cm$^4$/GW unit

EXAMPLE 18

Compound F-4 is used to demonstrate the emission quenching ability of different metal ions (Table 2). A range of metal ions, in addition to nickel, can be used to quench fluorescence emission from substituted phenanthroline compounds.

TABLE 2

The absorption and emission response of compound F-4 upon chelating with metal ions in chloroform/methanol (10:1)[a]

| Run | Metal ions | λ max (nm) | λ E$_M$ (nm) | Emission |
|---|---|---|---|---|
| 1 | Cu$^+$ | 368, 475 (shoulder) | / | quenched |
| 2 | Sn$^{2+}$ | 289, 394 (shoulder) | 526 | strong |
| 3 | Fe$^{3+}$ | Overlap with FeCl$_3$ | / | quenched |
| 4 | Ni$^{2+}$ | 350, 466 (shoulder) | / | quenched |
| 5 | Zn$^{2+}$ | 354, 451 (shoulder) | 505 | weak |
| 6 | Ion-free | 416 | 582 | strong |
| 7 | Ag$^+$ | 439, 340 (shoulder) | 665 | weak |

[a]The following metal salts were used: CuCl, NiCl$_2$, ZnCl$_2$, AgNO$_3$, SnCl$_2$, FeCl$_3$.

EXAMPLE 19

This example shows the ability of metal liganding to shift the TPA peak to lower energies and quench TPA fluorescence.

TPA spectra were obtained by using a single femtosecond white-light continuum generation beam and the direct degenerate TPA measurement technique. The continuum was generated in a 2.5 cm×2.5 cm right-angle quartz prism pumped by ~775 nm and ~160 fs laser pulses at 1 kHz repetition rate. The underlying principle and technical details of this TPA spectral measurement technique have been previously described (9).

The TPA bands for metal-ion chelating complexes are red-shifted compared to corresponding metal-ion free chromophores. The intrinsic maximum TPA cross-section values for F-2, M-2, F-3, M-3, F-4 and M-4 are $\sigma_2$=0.58, 2.21, 0.61, 2.26, 1.59 and 2.50 (±15%)×10$^{-20}$ cm$^4$/GW, respectively. These values are comparable to that of AF-350 and AF 389, which are highly active two-photon absorbing chromophores.

Figure 12:
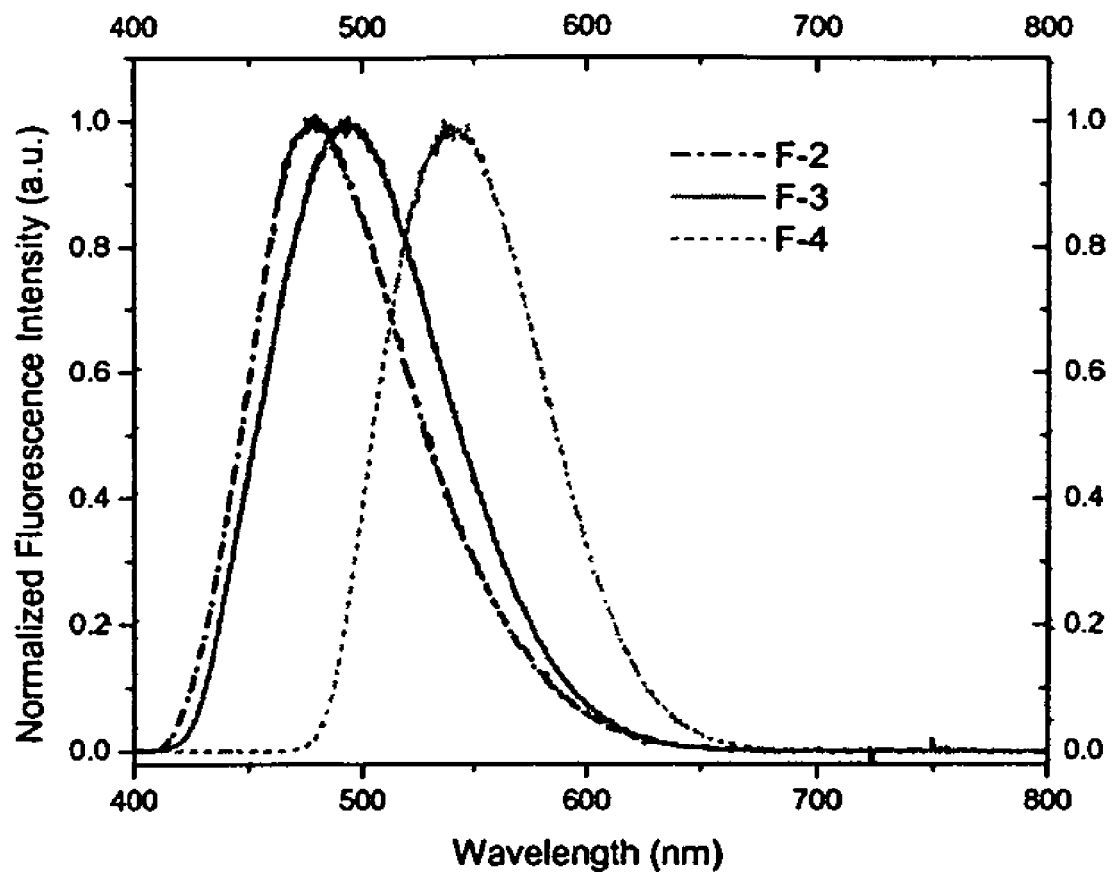
FIG. 12. Two-photon excited fluorescence spectra for compounds F-2,F-3, F-4; No detectable fluorescence found for compounds M-2, M-3, M-4.

As shown in FIG. 12, compounds F-2, F-3 and F-4 possess strong two-photon fluorescence (Excited by an 800 nm laser beam). However, there is no detectable two-photon fluorescence for compounds M-2, M-3 and M-4.

REFERENCES 1. (a) Van Stryland, E. W.; Wu, Y. Y.; Hagan, D. J. Soileau, M. J.; Mansour, K. *J. Opt. Soc. Am. B* 1988, 5, 1980. (b) Bhawalkar, Jayant D.; He, Guang S.; Prasad, Paras N. *Opt. Commun.* 1995, 119, 587. (c) Spangler, Charles W. *J. Mater. Chem.* 1999, 9, 2013. (d) Perry, J. W.; Mansour, K.; Lee, I.-Y. S.; Wu. X.-L.; Bedworth, P. V.; Chen, C.-T.; Ng, D.; Marder, S. R.; Miles, P.; et al. *Science.* 1996, 273, 1533.
2. (a) Mukheijee, Anadi. *Appl. Phys. Lett.* 1993, 62, 3423. (b) He, Guang S.; Zhao, Chan F.; Bhawalkar, Jayant D.; Prasad, Paras N. *Appl. Phys. Lett.* 1995, 67, 3703. (c) Zhao, Chan F.; Gvishi, Raz; Narang, Upvanu; Ruland, Gary; Prasad, Paras N. *J. Phys. Chem.* 1996,100,4526.
3. (a) Parthenopolous, D. A.; Rentzepis, P. M. *Science* 1989, 245, 843. (b) Pudavar, H. E.; Joshi, M. P.; Prasad, P. N.; Reinhardt, B. A. *Appl. Phys. Lett.* 1999, 74, 1338. (c) Cumpston, B. H.; Ananthavel, S. P.; Barlow, S.; Dyer, D. L.; Ehrlich, J. E.; Erskine, L. L.; Heikal, A. A.; Kuebler, S. M.; Lee, I. Y. S.; McCord-Maughon, D.; Qin, J. Q.; Rockel, H.; Rumi, M.; Wu, X. L.; Marder, S. R.; Perry, J. W. *Nature* 1999, 398, 51; (d) Belfield, K. D.; Liu, Y.; Negres, R. A.; Fan, M.; Pan, G.; Hagan, D. J.; Hernandez, F. E. *Chem. Mater.* 2002, 14, 3663.
4. (a) Bhawalkar, J. D.; Kumar, N. D.; Zhao, C. F.; Prasad, P. N. *J. Clin. Med. Surg.* 1997, 37, 510. (b) Frederiksen, P. K.; Jørgensen, M.; Ogilby, P. R. *J. Am. Chem. Soc.* 2001, 123, 1215.
5. He, Guang S.; Yuan, Lixiang; Bhawalkar, Jayant D.; Prasad, Paras N. *Appl. Opt.* 1997, 36, 3387.
6. Cumptson B.; Lipson M.; Marder S. R.; Perry J. W. 1999, WO 9953242.
7. (a) Porres L; Mongin O.; Katan C.; Charlot M.; Pons T.; Mertz J.; Blanchard-Desce, M. *Org. Lett.* 2004, 6, 47 (b) Kannan R.; He G. S.; Lin. T; Prasad P N.; Vaia R. A.; Tan L. S. *Chem. Mater.* 2004, 16, 185-194. (c) Beljonne D.; Wenseleers W.; Zojer E.; Shuai Z.; Vogel H.; Pond S J. K.; Perry J. W.; Marder S.R.; Bredas J. *Adv. Funct. Mater.* 2002, 12, 631-641 (d) Cho, Bong Rae; Piao, Ming Jun; Son, Kyung Hwa; Lee, Sang Hae; Yoon, Soo Jung; Jeon, Seung-Joon; Cho, Minhaeng. *Chem.—A Eur. J.* 2002, 8, 3907 (e) Lee W.; Lee H.; Kim, J.; Choi, J.; Cho, M.; Jeon, S.; Cho, B. *J. Am. Chem. Soc.* 2001, 123, 10658.
8. (a) Gillies E. R. and Frechet J. M. J. *J. Am. Chem. Soc.* 2002, 124, 14137. (b) Grayson S. M.; Frechet J. M. *J. Chem. Rev.* 2001, 101,3819.
9. He G. S; Lin T-C and Prasad P. N. Optics Express, 2002, 13, 566

The invention claimed is:

1. A compound having the following structure:

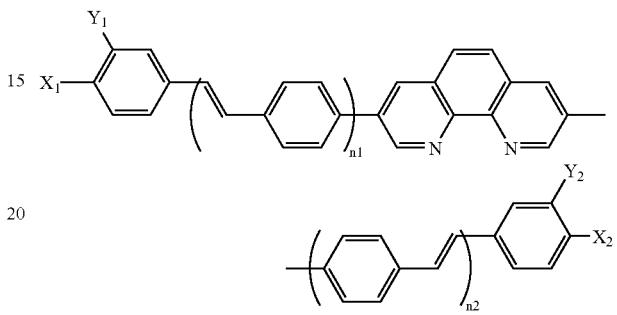

wherein $X_1$, $Y_1$, $X_2$ and $Y_2$ independently are either hydrogen or electron donating groups, wherein the electron donating groups are selected from the group consisting of SR1, OR2, NR3R4, and wherein R1, R2, R3, and R4 independently are hydrogen, hydroxyalkyl sulfoalkyl, carboxylalkyl, or unsubstituted alkyl groups; and wherein n1 and n2 independently are integers in the range of 1 to 10.

2. A compound as in claim 1 wherein $X_1$=$X_2$=SR1 and $Y_1$=$Y_2$=H, and wherein R1 is a hydrogen, hydroxyalkyl, sulfoalkyl, carboxyalkyl or unsubstituted alkyl group having in the range of from 1 to 20 carbons.

3. A compound as in claim 1 wherein $X_1$=$X_2$=$Y_1$=$Y_2$=OR2, and wherein R2 is hydrogen, hydroxyalkyl, sulfoalkyl, carboxyalkyl or unsubstituted alkyl groups having in the range of from 1 to 20 carbons.

4. A compound as in claim 1 wherein $X_1$=$X_2$=NR3R4 and $Y_1$=$Y_2$=H, and wherein R3 and R4 are independently hydrogen, hydroxyalkyl, sulfoalkyl, carboxyalkyl or unsubstituted alkyl groups having in the range of from 1 to 20 carbons.

5. A compound as in claim 2, wherein the phenanthroline nitrogens are coordinated to a transition metal ion and n l and n2 are 1.

6. A compound as in claim 3, wherein the phenanthroline nitrogens are coordinated to a transition metal ion and n1 and n2 are 1.

7. A compound as in claim 4, wherein the phenanthroline nitrogens are coordinated to a transition metal ion and n1 and n2 are 1.

8. A compound as in claim 6, wherein the metal ion is coordinated to identical phenanthroline-containing compounds.

9. A compound as in claim 7, wherein the metal ion is coordinated to identical phenanthroline-containing compounds.

10. A compound as in claim 1, wherein said compound has a two-photon absorption cross section at 800 nm which is greater than 2.33*10$^{-20}$cm$^4$/GW.

Figure 4:
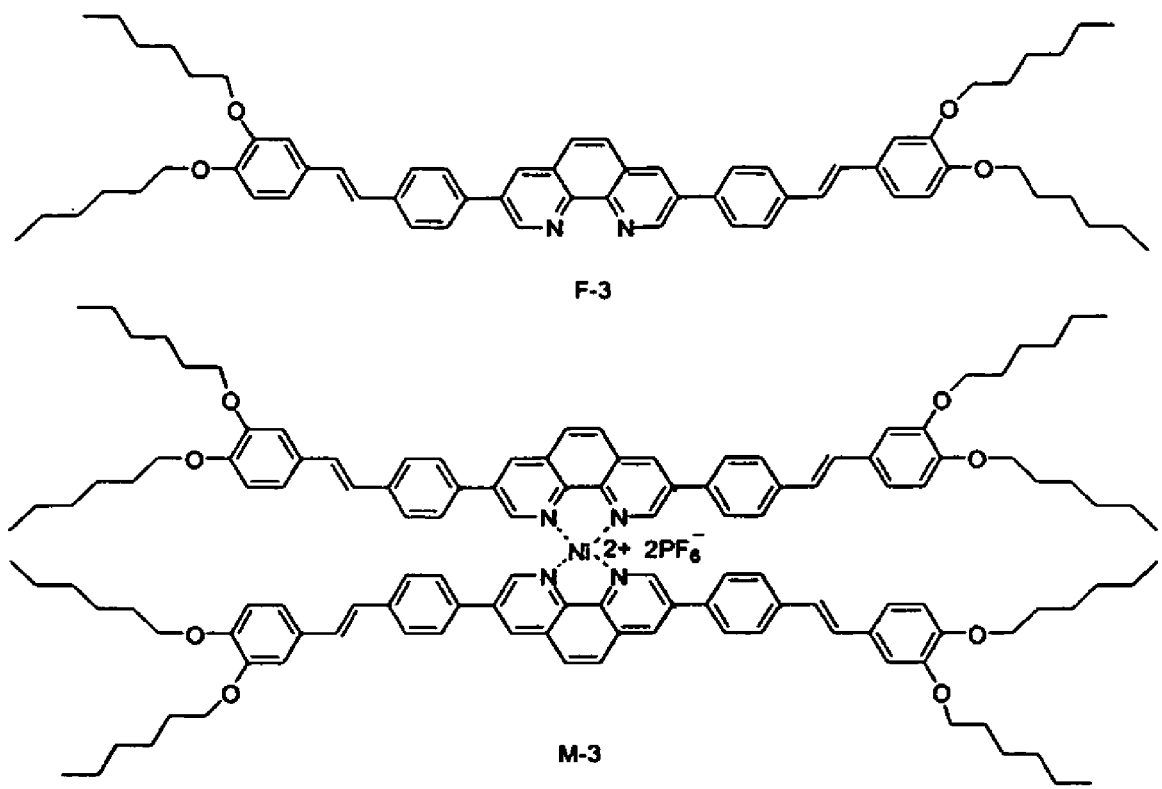
FIG. 4. Compounds F-3, M-3

11. A method for storing information in a three dimensional medium, said method comprising:

a) providing a three dimensional medium comprising a compound of the following structure, wherein n1 and n2 independently are integers in the range of 1 to 10; wherein $X_1$, $X_2$, $Y_1$ and $Y_2$ are independently H, SR1, OR2 or NR3R4, and wherein the R1, R2, R3, and R4 groups are independently hydrogen, hydroxyalkyl, sulfoalkyl, carboxyalkyl or unsubstituted alkyl group having in the range of from 1 to 20 carbons; M is a transition metal ion; and L is a ligand which is coordinated with the transition metal ion; and 15. A method as in claim 11 wherein said compound is M-3 of FIG. 4.

Figure 5:
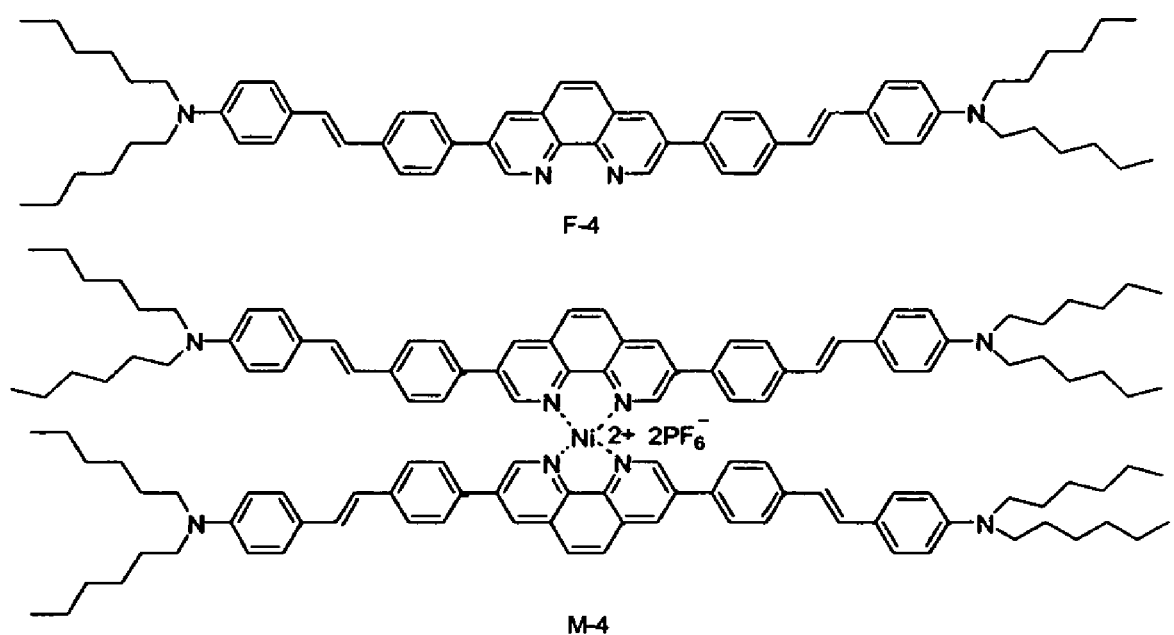
FIG. 5. Compounds F-4, M-4
Figure 6:
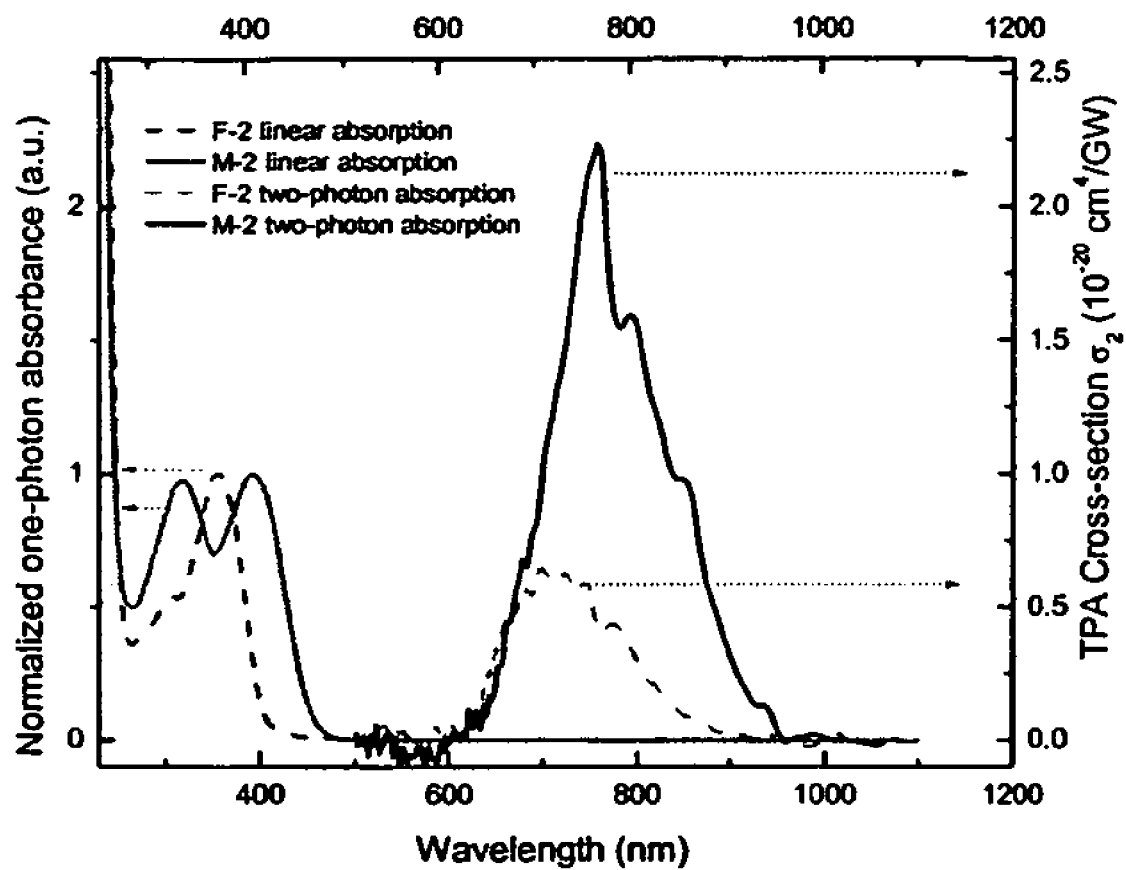
FIG. 6. One and two photon absorption spectra for compounds F-2, M-2
Figure 7:
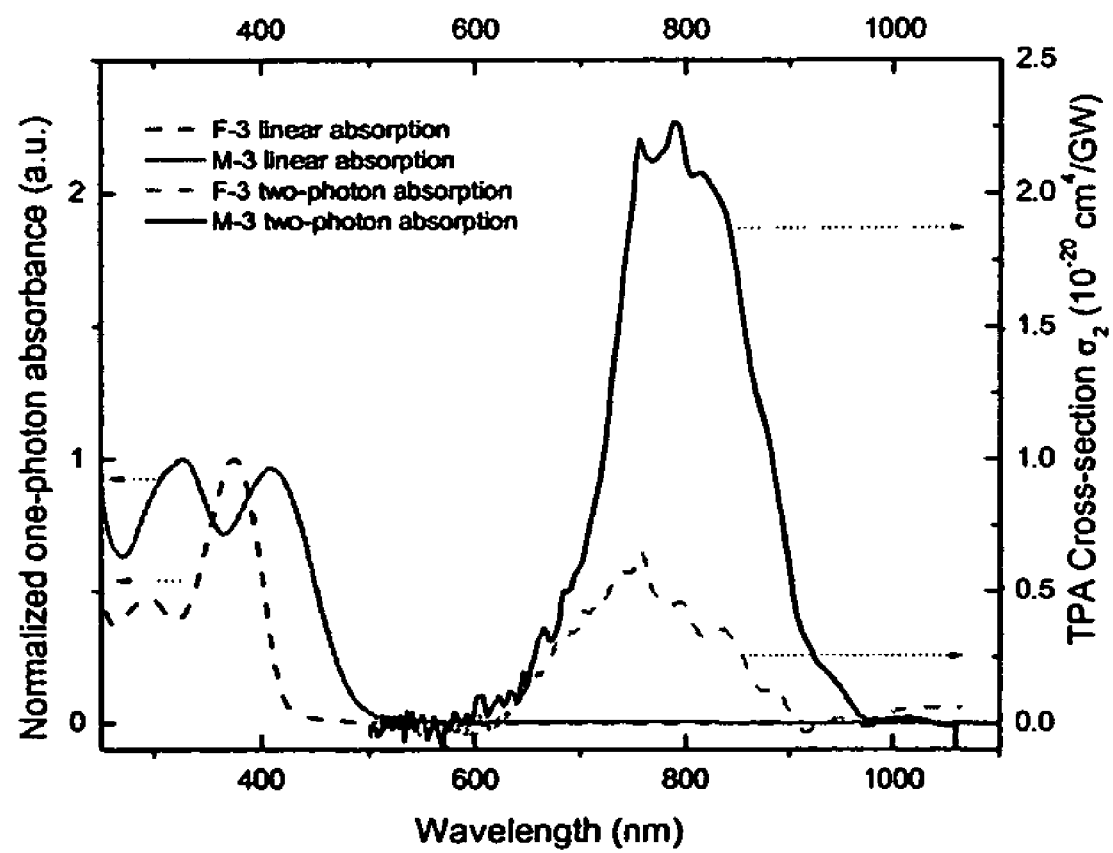
FIG. 7 One and two photon absorption spectra for compounds F-3, M-3
Figure 8:
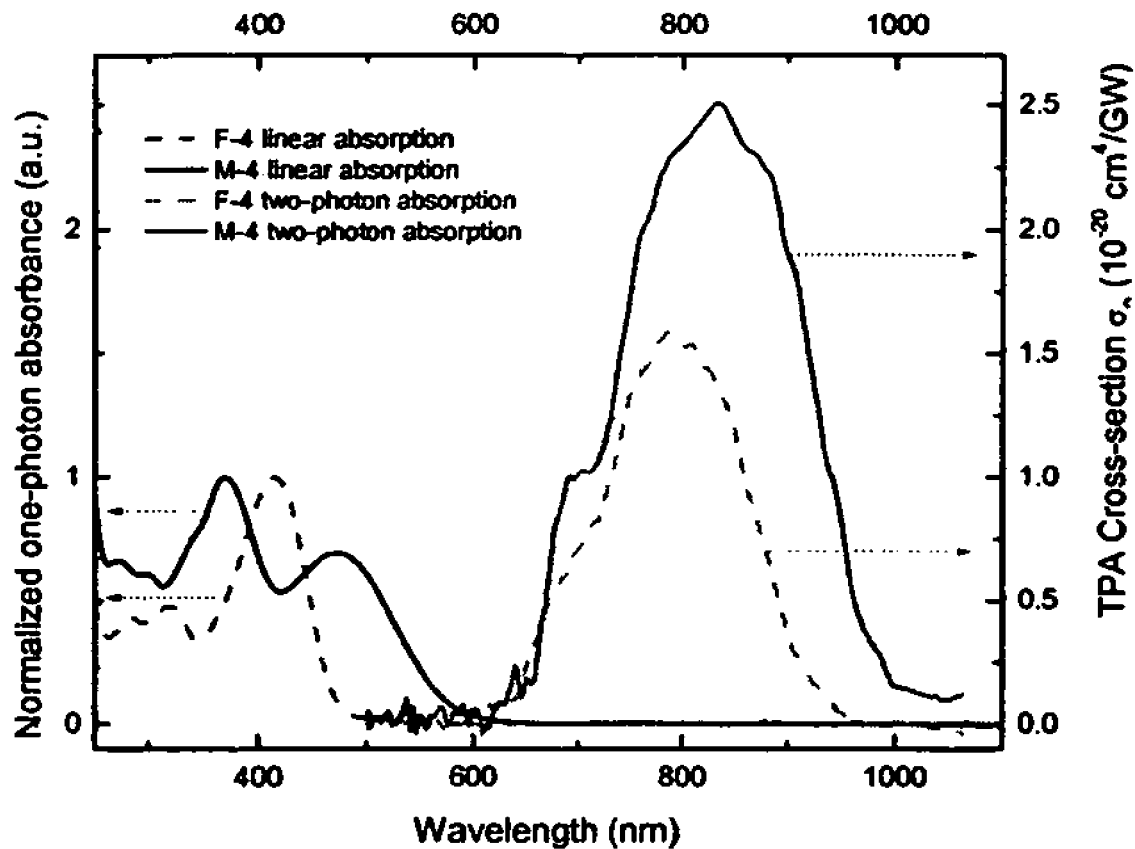
FIG. 8. One and two photon absorption spectra for compounds F-4, M-4

16. A method as in claim 11 wherein said compound is M-4 of FIG. 5.

17. A method of upconverting one or more wavelengths of radiation in the range of from 600 to 1000 nm, said method comprising:

a) providing a medium comprising a compound of claim 1;

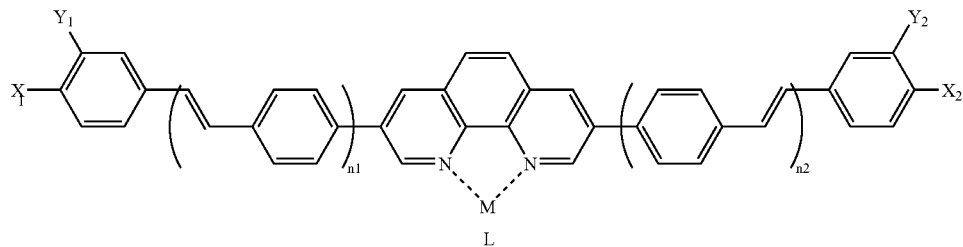

b) training a diverging beam comprising radiation of one or more wavelengths in the range of from 600 to 1000 nanometers into said medium, wherein said compound undergoes two photon absorption.

12. A method as in claim 11 wherein M is a transition metal selected from the group consisting of Nickel, Copper, Palladium, Ruthenium, Zinc, Iridium, Iron, and Silver.

13. A method as in claim 12 wherein L has the following structure:

b) exposing said compound to one or more wavelengths in the range of from 600 to 1000 nm such that the compound fluoresces radiation in the range of from 400 to 700 nm.

Figure 2:
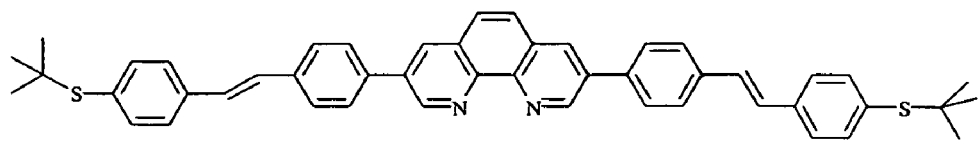
FIG. 2. Examples for the model
Figure 2:
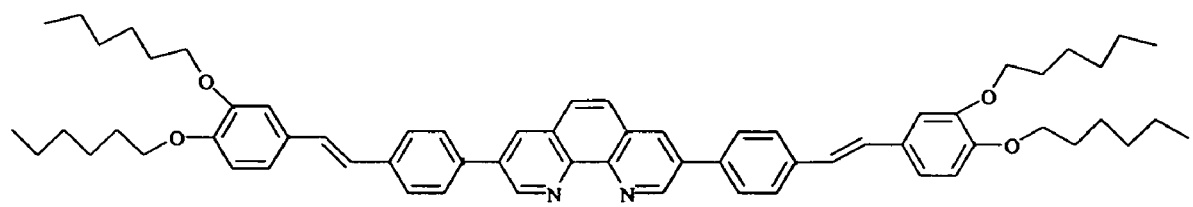
Figure 2:
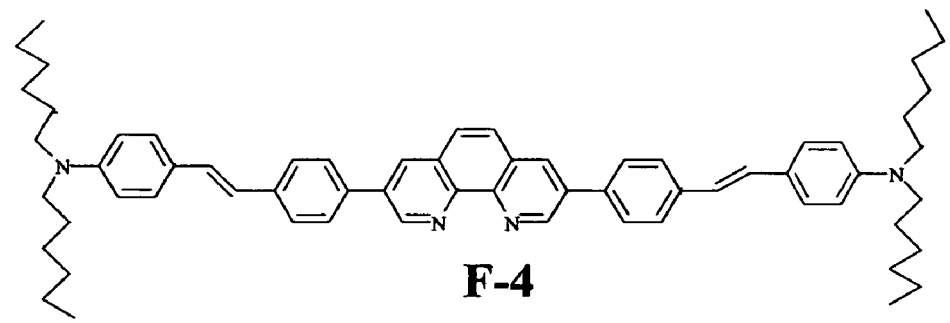

18. A method as in claim 17 wherein said compound is F2 of FIG. 2.

19. A method as in claim 17 wherein said compound is F3 of FIG. 2.

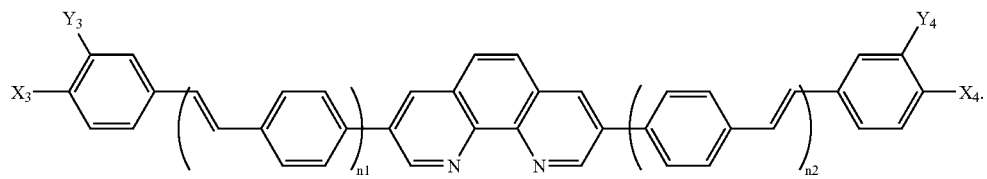

wherein n1 and n2 independently are integers in the range of 1 to 10; $X_3$, $X_4$, $Y_3$ and $Y_4$ are independently H, SR5, OR6 or NR7R8, and wherein R5, R6, R7 and R8 are independently hydrogen, hydroxyalkyl, sulfoalkyl, carboxyalkyl or unsubstituted alkyl groups having in the range of from 1 to 20 carbons.

Figure 3:
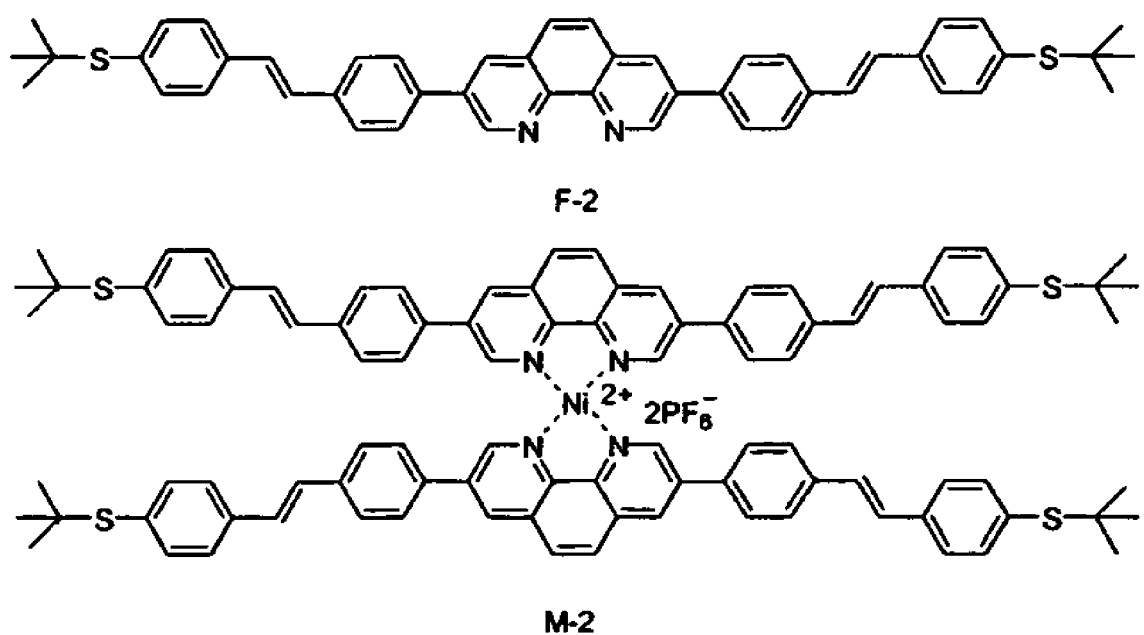
FIG. 3. Compounds F-2, M-2

14. A method as in claim 11 wherein said compound is M-2 of FIG. 3.

20. A method as in claim 17 wherein said compound is F4 of FIG. 2.

21. A compound as in claim 5, wherein the metal ion is coordinated to identical phenanthroline-containing compounds.

22. A method as in claim 17 wherein n1=n2; and wherein $X_1$=$X_2$, $Y_1$=$Y_2$, and wherein the alkyl groups have in the range from 1 to 20 carbons.

* * * * *